United States Patent
Humphrey et al.

(10) Patent No.: US 6,878,848 B2
(45) Date of Patent: Apr. 12, 2005

(54) PROCESS FOR CONVERTING A CIS-TRANS MIXTURE OF SUBSTITUTED BENZYLIDENE AMINES INTO THE PURE CIS ISOMER

(75) Inventors: John Michael Humphrey, Mystic, CT (US); Norma Jacqueline Tom, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/705,466

(22) Filed: Nov. 10, 2003

(65) Prior Publication Data

US 2004/0254380 A1 Dec. 16, 2004

Related U.S. Application Data

(60) Provisional application No. 60/425,946, filed on Nov. 12, 2002.

(51) Int. Cl.$^7$ .............................................. C07B 57/00
(52) U.S. Cl. ....................................... 564/303; 564/304
(58) Field of Search ................................. 564/303, 304

(56) References Cited

FOREIGN PATENT DOCUMENTS

WO           01/77100 A2 * 10/2001   ......... C07D/401/00

\* cited by examiner

*Primary Examiner*—Brian J. Davis
(74) *Attorney, Agent, or Firm*—P. C. Richardson; R. L. Catania; S. P. Suskind

(57) ABSTRACT

A process for interconverting a mixture of cis-trans isomers of a compound of formula I into the substantially pure cis isomer.

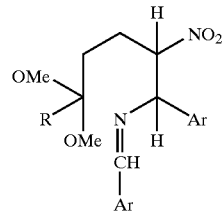

Cis isomers of formula I are useful intermediates in the synthesis of cis isomers of benzamide piperidine compounds which exhibit activity as NK-1 receptor antagonists.

24 Claims, No Drawings

PROCESS FOR CONVERTING A CIS-TRANS MIXTURE OF SUBSTITUTED BENZYLIDENE AMINES INTO THE PURE CIS ISOMER

This application claims benefit to U.S. Provisional No. 60/425,946 filed Nov. 12, 2002.

BACKGROUND OF THE INVENTION

The present invention provides a process for preparing a pure cis isomer from a mixture of cis-trans isomers of substituted benzylidene amines.

Substituted benzylidene amines of this invention, more specifically defined by formula I below, are useful intermediates in the preparation of benzamide piperidine compounds which exhibit activity as NK-1 receptor antagonists. The present synthesis of the cis isomer provides a new stereospecific pathway to the more biologically active cis benzamide piperidine in high yield.

A stereoselective route to a cis enriched benzamide piperidine was disclosed in WO 01/77100 which is U.S. patent application Ser. No. 09/811,218 filed on Mar. 16, 2001 and is incorporated herein by reference in its entirety. The resolution of the isomer enriched mixture into the desired pure isomer required additional steps accompanied by loss of valuable product. The present invention provides an alternate and more direct method for establishing the cis stereochemistry.

SUMMARY OF THE INVENTION

The present invention provides a method for preparing a pure cis isomer from a mixture of cis-trans isomers of formula

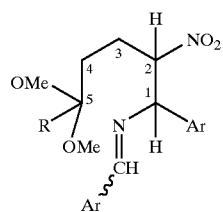

wherein R is $C_{1-5}$ alkyl and Ar is phenyl or naphthyl optionally mono-or di-substituted by $C_{1-5}$ alkyl, $C_{1-5}$ alkoxy, halogen, trifluoromethyl, ester, or amido; comprising the steps of a. dispersing a mixture of cis and trans isomers of formula I in an inert solvent in which said cis isomer is substantially less soluble in said solvent than said trans isomer;

b. heating said dispersion to completely dissolve said trans isomer and dissolve at least 10% by weight of the cis isomer;

c. maintaining said heating step to allow interconversion of said cis and trans isomers;

d. cooling said mixture thereby crystallizing the cis isomer; and e. separating said crystalline cis isomer from said solvent.

The method involves a sequence of steps starting with a dispersion of the isomer mixture in a selected solvent in which the cis isomer has lower solubility than the trans isomer. The initial dispersion is then heated and maintained at a suitable temperature and for a sufficient period of time to create a solution equilibrium whereby the isomers are interconvertible.

Heat is applied to the dispersion and maintained over an extended period in order to dissolve at least about 10% by weight of the cis isomer and establish an equilibrium of interconverting cis and trans isomers. In a preferred embodiment, the trans isomer is completely dissolved and at least a portion of the cis isomer is dissolved during the heating steps. In a preferred embodiment the equilibrium ratio of cis to trans isomers in solution is 3:1 during the heating step.

Upon cooling the solution, the less soluble cis isomer separates into a pure crystalline form.

The initial mixture of cis and trans isomers in step (a) above is provided in a weight ratio of cis to trans of about 60:40 to about 40:60. In a preferred embodiment the ratio is 50:50.

Suitable solvents are those in which the trans isomers dissolve completely at a temperature of about 30° C. The cis isomer, in the same solvent precipitates as a crystalline solid at a temperature of about 30° C. to about 40° C.

Suitable solvents are selected from the group consisting of an alcohol having formula $R^1OH$, a mixture of alcohols having formula $R^1OH$, and a mixture of one or more alcohols of formula $R^1OH$ with water, wherein $R^1$ is $C_1-C_5$ alkyl.

The preferred solvent is methyl alcohol.

After dispersing the mixture of cis-trans isomers in a solvent, the mixture is heated to a temperature of about 40° C. to about 55° C. and maintained for a period of at least 4 hours. Preferably the mixture is heated to a temperature of about 40° C. to about 45° C. for a period of about 7 hours.

In the next step, the mixture is allowed to cool slowly, thereby causing the less soluble cis isomer to separate as a crystalline solid. Generally, the mixture is cooled to a temperature of about 0° C. to about 35° C. over a period of about 96 hours; preferably the mixture is cooled to about 25° C. over a period of about 72 hours.

Finally the mixture is cooled to a temperature of about 0° C. to about 5° C. for a period of about 1 hour. At this stage, the solids are comprised of pure cis isomers.

Referring to formula I, both carbon atom $C_1$ and carbon atom $C_2$ are asymmetric carbon atoms and each create a stereocenter in molecule I.

Compounds of formula I contain two pairs of enantiomers. Between the two pairs, the enantiomers are diastereoisomeric and are generally expected to have different physical properties such as solubility in typical solvents.

The cis and trans isomers of the present invention refer to the configurational relationship of the nitro group and the aryl group on $C_2$ and $C_1$.

The interconversion of cis and trans isomers of the present invention is accounted for by the presence of a transition compound in which the $C_2$ carbon is achiral. The $C_2$ achiral carbon atom is formed by bond cleavage at the $C_2$ carbon atom. Preferably, bond cleavage takes place at the $C_2$—H bond whereby a proton $H^{\oplus}$ separates leaving a resonance stabilized carbanion at $C_2$. Reprotonation epimerizes the transition state back into either the cis or trans isomer.

The cleavage of a proton at the $C_2$ carbon atom is facilitated by the presence of an electron withdrawing group attached to $C_2$. Suitable electron withdrawing groups are selected from the group consisting of nitro, nitroso, nitrile, cyanato, isocyanto, nitrosubstituted aryl, sulfonyl, and carbonyl. Preferably the electron withdrawing group attached to $C_2$ is a nitro group.

In the present invention the cis configuration is favored and the solution equilibrium is maintained with heat at a ratio of cis-trans of 3:1 through the interconversion step.

Through the crystallization of the cis isomer and the shifting equilibrium via interconversion, the trans isomer is completely converted to the cis isomer.

DETAILED DESCRIPTION OF THE INVENTION

The invention provides a novel method for the preparation of the pure isomer through the interconversion of a mixture of the cis and trans isomers of a compound of formula I and the subsequent separation of the less soluble, more crystalline cis isomer.

In the present method a mixture of isomers is initially dispersed in an inert solvent and then partially or completely dissolved with the application of heat. An equilibrium is established between the dissolved isomers which are interconvertible through an achiral stereocenter. Through proper choice of solvent and appropriate heating and cooling conditions, the isomer mixture is completely converted to the cis configuration.

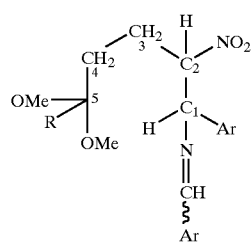

I

Stereochemical terms as found in the specification and claims herein are defined as follows:

An asymmetric atom is an atom that is bonded to four different atoms or groups. The location of an asymmetric atom is called a chiral center or stereocenter and a molecule containing one or more chiral centers is referred to as a chiral molecule. Chiral molecules are not identical with their mirror image and are not superimposable.

Isomers are compounds that have identical molecular formula, but differ in the nature, the sequence of bonding of their atoms, or in arrangement of their atoms in space. Stereoisomers are isomers that differ only in the arrangement of atoms in space. Enantiomers are stereoisomers which are mirror images of each other and are not superimposable. Diastereomers are stereoisomers that are not mirror images of each other. A racemate is a mixture of enantiomers present together in equal amounts.

Cis and trans isomers contain atoms or groups which project on the same side (cis) or an opposite sides (trans) of a reference plane. For diastereoisomers containing two asymmetric carbon atoms, the reference plane projects through both asymmetric atoms.

Epimerization is the reversible change of one diastereoisomer into another diastereoisomer.

Conversion is the non-reversible change of one stereoisomer to another.

In the present invention the structure of the cis and trans isomers relate to configuration around the stereocenters located at $C_1$ and $C_2$ in formula I. Specifically, the cis and trans configuration described herein relates to the spatial relationship between the $C_1$—Ar bond and the $C_2$—$NO_2$ bond.

In the initial step of the present invention the mixture of isomers is dispersed in a solvent in which the cis isomer has lower solubility than the trans isomers.

Heat is applied to the dispersion over an extended period in order to dissolve all of the trans isomer and at least a portion of the cis isomer. A solution equilibrium of cis and trans isomers is established which initially has a ratio of about 1:1. During the heating period the cis and trans isomers interconvert and the solution equilibrium shifts resulting in a cis to trans ratio of about 4:1 to about 3:1. In a preferred embodiment the equilibrium ratio of the cis to trans isomer in solution is 3:1.

During the cooling step, the more crystalline, less soluble cis isomer is precipitated from solution. The 3:1 equilibrium ratio in the solution is reestablished through further interconversion of the trans to the cis isomer. The process of slow cooling is continued until the solids are substantially all cis isomer.

The interconversion of the cis and trans isomers occurs via a planar transition compound which is formed by the cleavage of a bond at $C_2$. In general, the formation of intermediate transition compounds is favored by stabilizing resonance structures.

In a preferred embodiment of the present invention, bond cleavage occurs between the $C_2$ carbon atom and the hydrogen atom to which it is attached resulting in detachment of a proton ($H^\oplus$) and the conversion of the $C_2$ carbon atom into a planar, achiral carbanion having the resonance structures $1_R$.

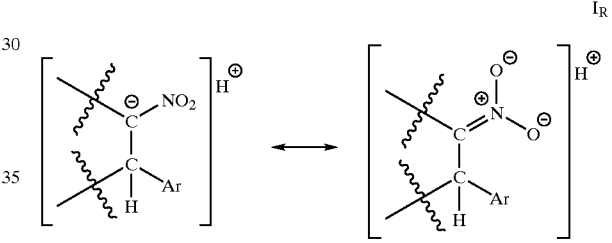

$I_R$

Resonance stabilization according to formula $I_R$ favors the formation of the planar carbanion. The removal of the H atom as the proton $H^\oplus$ at the $C_2$ carbon atom is facilitated by the neighboring nitro group making this an extremely labile hydrogen atom.

While not wishing to be held to theory, the inventors believe that the interconversion of isomers is best accounted for by chemical transformation at the achiral carbon atom $C_2$ in the transition state $I_R$. Specifically, reprotonation at $C_2$ results in either a cis or trans relationship between the nitro group at $C_2$ and the aryl group at $C_1$. The cis and trans isomers of I therefore exist in a solution equilibrium as illustrated in Scheme 1.

Generally, the heating step of the present invention takes place at a temperature of about 40° C. to about 55° C. and maintained for a period of at least 4 hours. The cooling step occurs at a temperature of about 0° C. to about 35° C. over a period of about 96 hours. In a preferred embodiment reprotonation at $C_2$ is favored for the cis configuration and so the solution equilibrium concentration of cis/trans is 3:1. Preferably the 3:1 ratio of cis/trans is maintained when the solution is held at a temperature about 40° C. to about 45° C. for a period of at least about 7 hours and the solvent is methyl alcohol. The mixture is next cooled preferably from 40° C. to about 35° C. for a period of about 10 hours and then cooled preferably from 35° C. to about 30° C. for a period of about 4 hours. Cooling continues preferably from 30° C. to about to 25° C. for a period of about 48 hours.

Finally, the mixture is cooled to about 0° C. to 5° C. for a period of about 1 hr. At this point the solids have been completely converted to the cis configuration.

The compounds represented by formula Ia and Ic are not mirror images of each other and are therefore diastereoisomeric; similarly, compounds Ia and Id, Ib and Ic, and Ib and Id are diastereoisomeric. Diastereoisomers ordinarily have different properties such as boiling point, melting point, and solubilities.

Referring to Figure 1, compounds of the present invention exist in both the cis configuration as illustrated by Ia and its enantiomer Ib and in the trans configuration as illustrated by Ic and its enantiomer Id.

Scheme 2 illustrates the procedure for the preparation of compounds of formula I in a 1:1 cis to trans ratio as disclosed in WO 01/77100.

In Scheme 2 nitromethane is added to an alkyl vinyl ketone to form a corresponding 1-nitro 4-oxo alkane, which reacts in a subsequent step with two equivalents of the aromatic aldehyde PhCHO in the presence of trimethylorthoformate, ammonium acetate as an amine source yielding the compound of formula I in approximately 1:1 cis to trans ratio.

SCHEME 1
Solution Equilibrium of the Cis and Trans Isomers of Formula I

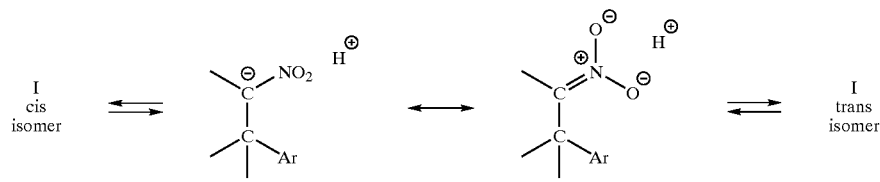

The compounds of formula I comprise a substituted ethane comprising carbon atom $C_1$ and carbon atom $C_2$ wherein $C_1$ is an asymmetric carbon atom with single bond attachments to 4 different substituents. The 4 substituents are —H, —Ar, —N=CH—Ar, and $C_2$. $C_2$ is a second asymmetric carbon atom with single bond attachments to —H, —$NO_2$, $C_1$ and —$(CH_2)_2C(OMe)_2R$. According to established chemical principals well known to those skilled in the art, compounds with n asymmetric atoms are comprised of a number of stereoisomers not exceeding $2^n$. Compounds of formula 1 contain $2^2$ or 4 stereoisomers Ia, b, c and d as represented by Figure 1.

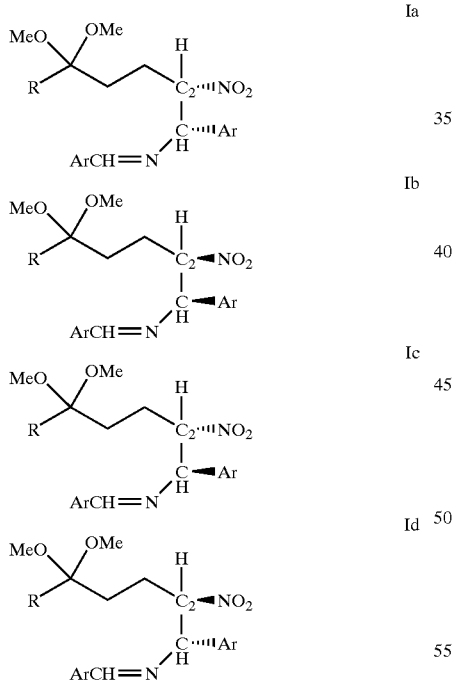

Compounds Ia to Id have the same molecular formula (i.e. each consists of the same substituents on $C_1$ and $C_2$ but all 4 differ in the arrangement of substituents on $C_1$ and $C_2$.

Compounds represented by formula Ia and Ib are a pair of enantiomers wherein each compound is the mirror-image of the other and wherein Ia and Ib are non-superimposable. Compounds Ic and Id are a second pair of enantiomers wherein each compound is the mirror-image of the other and wherein Ic and Id are non-superimposable.

SCHEME 2

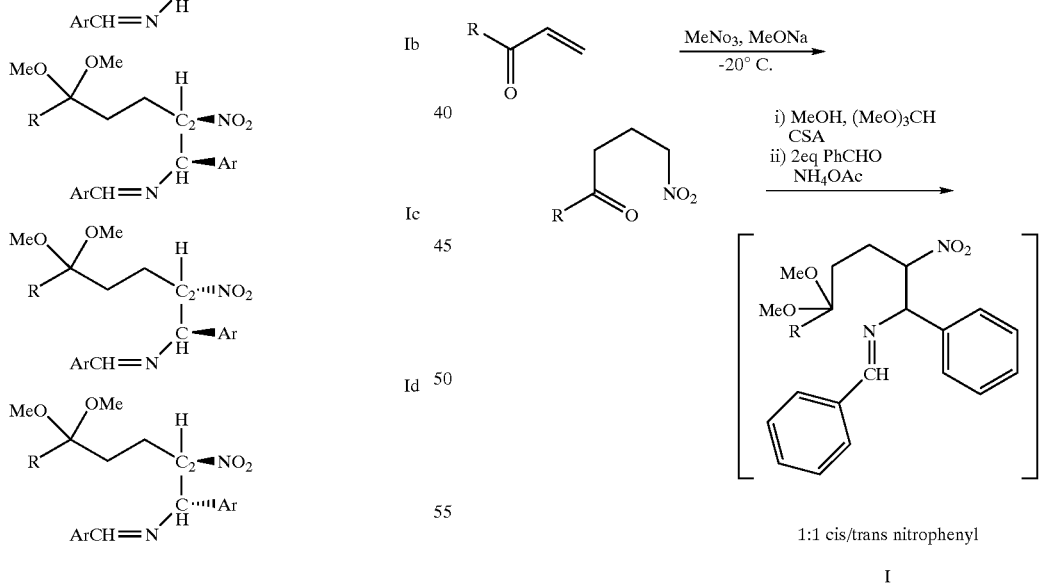

1:1 cis/trans nitrophenyl

I

As disclosed in WO01/77100 compounds of formula I, in the form of a mixture of cis and trans isomers including the racemate, are useful intermediates in the synthesis of certain cis enriched benzamide piperidine compounds which exhibit pharmaceutical activity in the treatment and prevention of central nervous system disorders. A representative benzamide piperidine compound is the compound having formula VI.

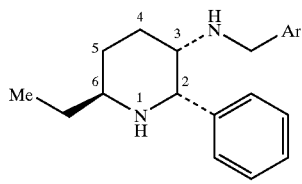

wherein the phenyl substituent on piperidine ring atom 2 and the amino substituent on ring atom 3 are in the cis configuration and wherein the alkyl group on ring atom 6 is in the trans configuration to the phenyl group on atom 2, and $Ar^1$ is selected from mono- or disubstituted aryl or heteroaryl.

Examples of specific compounds of the formula VI are the following compounds:

7-[(6-Isobutyl-2-phenyl-piperidin-3-ylamino)-methyl]-6-methoxy-1-methyl-3,4-dihydro-1H-quinolin-2-one;

6-Methoxy-3-methyl-5-[(6-methyl-2-phenyl-piperidin-3-ylamino)-methyl]-1,1a,3,7b-tetrahydro-3-aza-cyclopropa[a]naphthalen-2-one;

[1-(2-Dimethylamino-ethyl)-2-phenyl-piperidin-3-yl]-(2-methoxy-5-trifluoromethoxy-benzyl)-amine;

6-Methoxy-1-methyl-7-[(2-phenyl-octahydro-cyclopenta[b]pyrrol-3-ylamino)-methyl]-3,4-dihydro-1H-quinolin-2-one;

(2-Methoxy-5-trifluoromethoxy-benzyl)-(1-[1,2,4]oxadiazol-3-ylmethyl-2-phenyl-piperidin-3-yl)-amine;

7-{[1-(Imidazol-1-yl-acetyl)-2-phenyl-piperidin-3-ylamino]-methyl}-6-methoxy-1-methyl-3,4-dihydro-1H-quinolin-2-one;

6-Methoxy-3-methyl-5-[(6-methyl-2-phenyl-piperidin-3-ylamino)-methyl]-1,1a,3,7b-tetrahydro-3-aza-cyclopropa[a]naphthalen-2-one;

6-Methoxy-1-methyl-7-[6-ethyl-2-phenyl-pipidin-3-ylamino)-methyl]-3,4-dihydro-1H-1,1a,3,7b-terahydro-3-aza-cyclopropa[a]naphthalen-2-one;

6-Methoxy-1-methyl, 3,3-cyclopropyl-7-[6-ethyl-2-phenyl-piperidine-3-ylamino)-methyl]-1,3 dihydro-indol-2-one;

5-[(6-Ethyl-2-phenyl-piperidin-3-ylamino)-methyl]-6-methoxy-3-methyl-1,1a,3,7b-tetrahydro-3-aza-cyclopropa[a]naphthalen-2-one.

and pharmaceutically acceptable salts thereof.

According to the above cited reference, when a mixture of racemic diastereomers of formula I is an intermediate to VI, a stereoselective reduction in a subsequent step leads to cis enriched VI as illustrated in Scheme 3.

SCHEME 3

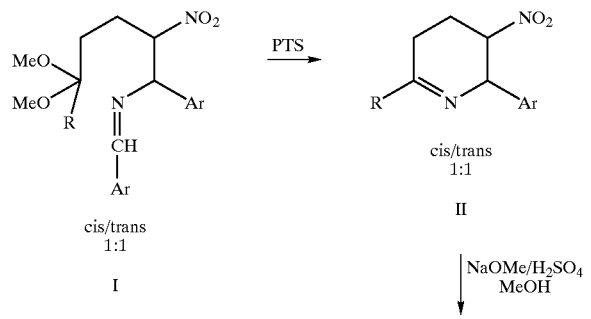

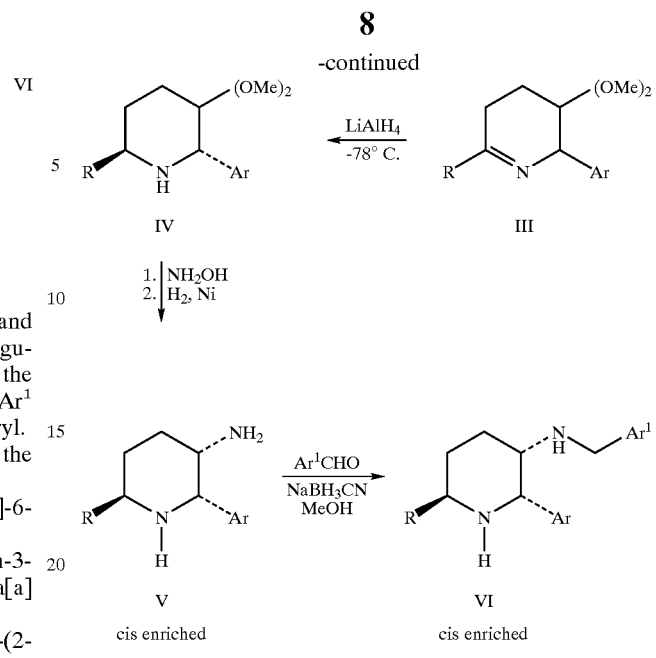

According to Scheme 3, compounds of formula I are converted to the cyclic imine III followed by reduction to the substituted piperidine IV with a hydrogen source such as lithium aluminum hydride in the presence of a Lewis acid such as trimethylaluminum at about −78° C. In the resulting piperidine IV, the ethyl group at the 6 position of the ring is desirably trans to the aryl group at position 2. Compounds of formula IV are converted to the oxime at the 3-position which is then stereospecifically reduced with hydrogen and Raney nickel to give the cis enriched configuration with respect to the Ar group on position 2. The cis configuration is retained through the final steps to the cis enriched compounds of formula VI. This route which employs the 1:1 mixture of cis/trans isomers of the formula I has the serious drawback of requiring multiple steps and purifications with accompanying yield loss to obtain compounds of the formula VI. The present inventors have recognized the need to produce pure cis isomers of the formula V, which in turn provides compounds of the formula VI with the desired stereochemistry, by a more direct, less costly method. The pure isomer of formula I provides a new method employing fewer steps for establishing and maintaining the desired cis stereochemistry.

Scheme 4 illustrates an alternate route to cis isomers of VI utilizing pure cis compounds I prepared according to the present invention. This new method, which is based upon a reaction sequence disclosed in WO01/77100, provides VI directly as the pure cis isomer with improved yield and fewer steps.

According to Scheme 4, cyclization of cis isomer I followed by nitrogen protection gives the cis enamine IIa. The subsequent steps of reduction and deprotection yields compounds of the formula V with the desired cis nitro phenyl stereochemistry.

SCHEME 4

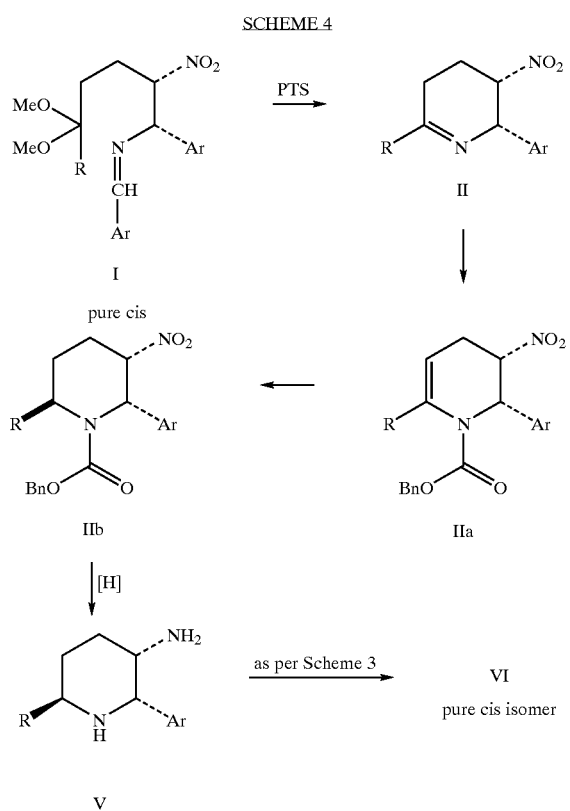

In a preferred embodiment of the invention the compound of formula I is benzylidene-(5,5-dimethoxy-2-nitro-1-phenyl-heptyl)-amine.

The compounds of formula VI, and the intermediates shown in the above reaction schemes can be isolated and purified by conventional procedures, such as recrystallization or chromatographic separation.

The compounds of the formula VI and their pharmaceutically acceptable salts can be administered to mammals via either the oral, parenteral (such as subcutaneous, intravenous, intramuscular, intrasternal and infusion techniques), rectal, intranasal or topical routes. In general, these compounds are most desirably administered in doses ranging from about 0.01 to about 1500 mg per day, in single or divided doses (i.e., from 1 to 4 doses per day), although variations will necessarily occur depending upon the species, weight and condition of the subject being treated and the particular route of administration chosen. However, a dosage level that is in the range of about 0.5 mg to about 500 mg per kg of body weight per day is most desirably employed. Nevertheless, variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such higher dose levels are first divided into several small doses for administration throughout the day.

The compounds of formula VI may be administered alone or in combination with pharmaceutically acceptable carriers or diluents by either of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar,type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of formula VI in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art.

Additionally, it is also possible to administer the compounds of the formula VI topically when treating inflammatory conditions of the skin and this may be done by way of creams, jellies, gels, pastes, patches, ointments and the like, in accordance with standard pharmaceutical practice.

The activity of the compounds of formula VI as substance P antagonists is determined by their ability to inhibit the binding of substance P at its receptor sites in IM-9 cells employing radioactive ligands. The substance P antagonist activity of the compounds described herein is evaluated by using the standard assay procedure described by D. G. Payan et al., as reported in the *The Journal of Immunology*, 133, 3260 (1984). This method essentially involves determining the concentration of the individual compound required to reduce by 50% the amount of radiolabelled substance P ligands at their receptor sites in said isolated cow tissues or IM-9 cells, thereby affording characteristic $IC_{50}$ values for each compound tested. More specifically, inhibition of [$^3$H] SP binding to human IM-9 cells by compounds are determined in assay buffer (50 mM Tris-HCl (pH 7.4), 1 mM $MnCl_2$, 0.02% bovine serum albumin, bacitracin (40 µg/ml), leupeptin (4 μg/ml), chymostatin (2 μg/ml) and phosphoramidon (30 μg/ml)). The reaction is initiated by the addition of cells to assay buffer containing 0.56 nM [$^3$H]SP and various concentrations of compounds (total volume 0.5 ml) and allowed to incubate for 120 min at 4° C. Incubation is terminated by filtration onto GF/B filters (presoaked in 0.1% polyethylenamine for 2 hours). Nonspecific binding is defined as the radioactivity remaining in the presence of 1 μM SP. The filters are placed into tubes and counted using liquid scintillation counter.

Compounds of formula VI were tested and at least one stereoisomer of each such compound exhibited a binding affinity, measured as $K_i$, of at least 600 nM.

The activity of the compounds of formula VI against generalized anxiety disorder can be determined by inhibition of GR73632-induced tapping test in gerbils. More specifically, gerbils are lightly anesthetized with ether and the skull surface is exposed. GR73632 or vehicle (PBS, 5 μl) are administered directly into the lateral ventricles via a 25 gauge needle inserted 4.5 mm below bregma (preceded by pretreatment with an antagonist, 0.1–32.0 mg/kg, s.c. or p.o.). Following injection, gerbils are placed in 1 L beaker individually and monitored for repetitive hind paw tapping. Some compounds prepared according to scheme 4 were tested in accordance with these testing methods. As a result, it was found that the compounds of formula VI have good antagonist activity toward substance P, particularly good activity against CNS disorders with decreased side effects.

The present invention is illustrated by the following examples. It will be understood, however, that the invention is not limited to the specific details of these examples. Melting points are uncorrected. Proton nuclear magnetic resonance spectra ($^1$H NMR) and $^{13}$C nuclear magnetic resonance spectra were measured for solutions in deuterochloroform (CDCl$_3$) or in CD$_3$OD or CD$_3$SOCD$_3$ and peak positions are expressed in parts per million (ppm) downfield from tetramethylsilane (TMS). The peak shapes are denoted as follows: s, singlet; d, doublet; t, triplet; q, quartet; m, multiplet; b, broad.

PREPARATION 1

6-nitro-hexan-3-one

A solution of sodium methoxide in MeOH (4.6M, 6.46 mL, 29.7 mmol, 0.25 equiv) was added to a solution of ethyl vinyl ketone (11.78 mL, 119 mmol, 1 equiv) and nitromethane (19.3 mL, 357 mmol, 3 equiv) in MeOH (30 mL, 3 vol) at −30° C. The reaction mixture was then warmed to −10° C. for 1.5 h, quenched with half saturated ammonium chloride solution (100 mL), and then extracted with dichloromethane (3×100 mL). The combined organics were dried over sodium sulfate, concentrated and then stripped from toluene (2×100 mL) and MeOH (100 mL) to provide 15.2 g of approximately 95% pure 6-nitro-hexan-3-one as determined by $^1$H NMR.

$^1$H NMR (CDC13) δ 4.32 (t, 2H, J=6.6 Hz), 2.46 (t, 2H, J=6.6 Hz), 2.32 (m, 2H), 2.12 (m, 2H), 0.92 (t, 3H, J=7.5 Hz).

PREPARATION 2

7-nitro-heptan-4-one

A solution of sodium methoxide in MeOH is added to a solution of 1-hexen-3-one and nitromethane in MeOH at −30° C. The reaction mixture is then warmed to −10° C. for 1.5 h, quenched with half saturated ammonium chloride solution, and then extracted with dichloromethane. The combined organics are dried over sodium sulfate concentrated and then stripped from toluene and MeOH to provide 7-nitro-heptan-4-one.

EXAMPLE 1

Cis-benzylidene-(5,5-dimthoxy-2-nitro-1-phenyl-beptyl)-amine

Camphorsulfonic acid (CSA, 1.11 g, 4.78 mmol, 0.05 equiv) was added to a solution of 6-nitro-hexan-3-one (13.9 g, 95.7 mmol, 1 equiv) from preparation 1 in MeOH (28 mL, 2 vol) and trimethyl orthoformate (28 mL, 2 vol), and the resulting solution was stirred at room temperature for 30 min. A solution of ammonium acetate (36.9 g, 478 mmol, 5 equiv) in MeOH (120 mL) and benzaldehyde (19.5 mL, 191 mmol, 2 equiv) was added and the solution was stirred at room temperature. After about 6 hours, crystals appeared. By $^1$H NMR, the solids were a 1:1 mixture of cis/trans benzylidene-(5,5-dimethoxy-2nitro-1-phenyl-heptyl)-amine. The reaction was then heated at 40° C. for 7 h. The solids were all cis benzylidene-(5,5-dimethoxy-2-nitro-1-phenyl-hepty)-amine. However, the filtrate still showed a mixture of cis and trans material. The reaction was cooled to 35° C. and stirred overnight, then was cooled to 30° C. for 4 h, and finally to room temperature. After stirring over the weekend, the reaction mixture was cooled to 0° C. The product was collected by filtration to afford 24.3 g (66%) of benzylidene-(5,5-dimethoxy-2-nitro-1phenyl-heptyl)-amine with only the cis nitrophenyl stereochemistry. The preceding steps are summarized in Table 1 below.

$^1$H NMR (CDC13) δ 8.2 (s, 1H), 7.72 (m, 1H), 7.35 (m, 8H), 5.03 (m, 1H), 4.65 (d, 1H, J=10 Hz), 3.04 (s, 3H), 2.98 (s, 3H), 1.50 (m, 4H), 1.42 (m, 2H), 0.65 (t, 3H, J=7.5 Hz).

EXAMPLE 2

Camphorsulfonic acid is added to a solution of 7-nitro-heptan-4-one from preparation 2 in MeOH and trimethyl orthoformate and the resulting solution is stirred at room temperature for 30 min. A solution of ammonium acetate in MeOH and benzaldehyde is added and the solution is stirred at room temperature for 6 h. The reaction is then heated at 40° C. for 7 h. The reaction is cooled to 35° C. and stirred overnight, then is cooled to 30° C. for 4 h, and finally to room temperature. After stirring over a weekend, the reaction mixture is cooled to 0° C. The product is collected by filtration to afford benzylidene-(5,5-dimethoxy-2-nitro-1phenyl-octyl)-amine with only the cis nitrophenyl stereochemistry.

EXAMPLE 3

Camphorsulfonic acid is added to a solution of 6-nitro-hexan-3-one from preparation 1 in MeOH (28 mL, 2 vol) and trimethyl orthoformate, and the resulting solution is stirred at room temperature for 30 min. A solution of ammonium acetate in MeOH and 4-chlorobenzaldehyde is added and the solution is stirred at room temperature for 6 hours. The reaction is then heated at 40° C. for 7 h. The reaction is cooled to 35° C. and stirred overnight, then is cooled to 30° C. for 4 h, and finally to room temperature. After stirring over a weekend, the reaction mixture is cooled to 0° C. The product is collected by filtration to afford (4-chloro-benzylidene)-[1-(4-chloro-phenyl)-5,5-dimethoxy-2nitro-heptyl]-amine with only the cis nitrophenyl stereochemistry.

EXAMPLE 4

Camphorsulfonic acid was added to a solution of 6-nitro-hexan-3-one from preparation 1 in MeOH and trimethyl orthoformate, and the resulting solution is stirred at room temperature for 30 min. A solution of ammonium acetate in MeOH and benzaldehyde was added and the solution is stirred at room temperature overnight. The reaction was then heated at reflux for 3–4 h. The reaction was cooled to 50° C. for 8 h, then was cooled to 30° C. for 8 h, and finally to room temperature for 8 h. After stirring over the weekend, the reaction mixture was cooled to 0° C. for 1 h. The product is collected by filtration to afford benzylidene-(5,5-dimethoxy-2-nitro-1-phenyl-hepty)-amine with only the cis nitrophenyl stereochemistry.

EXAMPLE 5

Camphorsulfonic acid was added to a solution of 6-nitro-hexan-3-one from preparation 1 in isopropanol and trimethyl orthoformate, and the resulting solution is stirred at room temperature for 30 min. A solution of ammonium acetate in isopropanol and benzaldehyde is added and the solution is stirred at room temperature for 6 hours. The reaction is then heated at 40° C. for 7 h. The reaction was cooled to 35° C. and stirred overnight, then was cooled to 30° C. for 4 h, and finally to room temperature. After stirring over the weekend, the reaction mixture was cooled to 0° C. The product was collected by filtration to afford benzylidene-(5,5-dimethoxy-2-nitro-1-phenyl-hepty)-amine with only the cis nitrophenyl stereochemistry.

Interconversion of Cis/Trans- to Pure Cis

TABLE 1

| PROCESS STEPS | SOLIDS | SOLUTION |
| --- | --- | --- |
| Start Time | None | cis/trans isomers and enantiomers |
| Stirring 6 hours 25° C. | cis/trans isomers and enantiomers | cis/trans isomers and enantiomers |
| Heating 7 hours 40° C. | cis isomer and enantiomers | cis/trans isomers and enantiomers ratio ~3:1 cis/trans |
| Cooling 10 hours 35° C. | Additional Cis isomer and enantiomers | cis/trans isomers and enantiomers Initial ratio <3:1 cis/trans Equilibrium ratio ~3:1 cis/trans |
| Cooling 4 hours 30° C. | Additional Cis isomer and enantiomers | cis/trans isomers and enantiomers Initial ratio <3:1 cis/trans Equilibrium ratio ~3:1 cis/trans |
| Cooling 48 hours 25° C. | Additional Cis isomer and enantiomers | cis/trans isomers and enantiomers Initial ratio <3:1 cis/trans Equilibrium ratio ~3:1 cis/trans Only small amounts of product left in solution |
| Cooling 1 hours 0° C. | Additional Cis isomer and enantiomers | Very little product left in solution |

We claim:

1. A process for preparing a pure cis isomer from a mixture of cis-trans isomers of formula

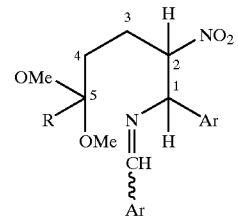

wherein Ar is phenyl or naphthyl optionally mono- or disubstituted by $C_{1-5}$ alkyl, $C_{1-5}$ alkoxy, halogen, trifluoromethyl, ester or amido; and R is $C_{1-5}$ alkyl;

wherein X is a strongly electron withdrawing moiety selected from the group consisting of nitro, nitroso, nitrilo, isocyanato, sulfonyl, carbonyl and nitro substituted aryl;

comprising the steps of:
a. dispersing a mixture of cis and trans isomers of formula I in an inert solvent wherein said cis isomer is substantially less soluble than said trans isomer;
b. heating said dispersion to completely dissolve said trans isomer and to dissolve at least 10% by weight of the cis isomers;
c. maintaining said heating step to allow interconversion of said cis and trans isomers;
d. cooling said mixture thereby crystallizing the cis isomer; and
e. separating said crystalline cis isomer from said solvent.

2. The process according to claim 1 wherein X is nitro.

3. The process according to claim 1 wherein said interconversion of the cis and trans isomers involves bond cleavage and reforming at carbon atom $C_2$.

4. The process of claim 3 wherein said bond cleavage and reforming takes place at the bond between carbon atom $C_2$ and its attached hydrogen atom.

5. The process of claim 4 wherein said bond cleavage results in an achiral transition compound having resonance formula;

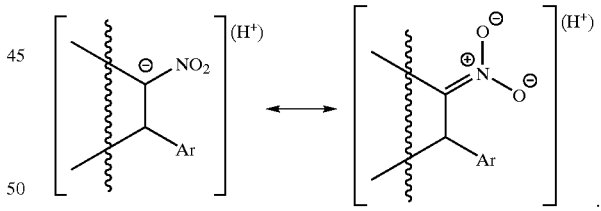

6. The process of claim 5 wherein said cis and trans isomers in said solvent interconvert through said transition compound.

7. The process of claim 1 wherein said crystallization of the cis isomer results in a further interconversion of the dissolved trans isomer into the cis isomer.

8. The process according to claim 1 wherein said dispersed cis and trans isomer mixture is comprised of solid cis and trans isomers in a weight ratio of about 1:1.

9. The process according to claim 4 wherein at least a portion of said cis and trans isomers are present in a solution equilibrium of said cis and trans isomer in a ratio of 3:1.

10. The process according to claim 1 wherein said mixture is heated to a temperature range of about 40° C. to about 55° C.

11. The process according to claim 10 wherein said mixture is heated to a temperature range of about 40° C. to about 45° C.

12. The process according to claim 1 wherein said heating step continues for a period of at least one hour.

13. The process of claim 10 wherein said heating step continues for a period of about 4 to about 10 hours.

14. The process of claim 1 wherein said mixture is cooled to a temperature of about 0° C. to about 35° C.

15. The process according to claim 1 wherein R is $C_1$–$C_3$ alkyl.

16. The process according to claim 1 wherein Ar is phenyl.

17. The process according to claim 1 wherein said compound of formula I is benzylidene-(5,5-dimethoxy-2-nitro-1-phenyl-heptyl)-amine.

18. The process according to claim 1 wherein said inert solvent is selected from the group consisting of an alcohol having formula $R^1OH$, a mixture of alcohols having formula $R^1OH$, and a mixture of water with one or more alcohols of formula $R^1OH$ wherein $R^1$ is $C_1$–$C_5$ alkyl.

19. The process according to claim 18 wherein said solvent is methanol.

20. The process according to claim 1 wherein said mixture is comprised of four stereoisomers.

21. The process according to claim 20 wherein said four stereoisomers are comprised of two pair of enantiomers.

22. The process according to claim 21 wherein a first pair of enantiomers consists of a cis isomer and its mirror image and a second pair of enantiomers consists of a trans isomer and its mirror image.

23. The process of claim 22 wherein said cis isomer and said trans isomer are diastereoisomers.

24. The process according to claim 1 wherein said cis and trans isomers are interconverted through transition compounds having the resonance formulas,

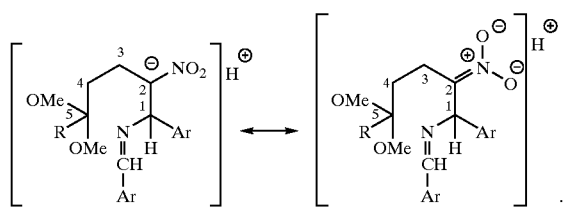

* * * * *

UNITED STATES PATENT AND TRADEMARK OFFICE
CERTIFICATE OF CORRECTION

PATENT NO. : 6,878,848 B2
DATED : April 12, 2005
INVENTOR(S) : John Michael Humphrey et al.

It is certified that error appears in the above-identified patent and that said Letters Patent is hereby corrected as shown below:

Column 14,
Lines 1-10, should read

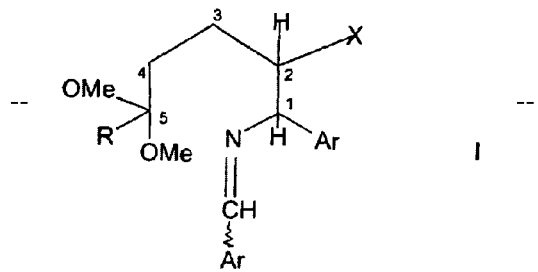

Signed and Sealed this

Twenty-third Day of August, 2005

JON W. DUDAS
*Director of the United States Patent and Trademark Office*